United States Patent [19]

Nakagawa et al.

[11] Patent Number: 4,707,241

[45] Date of Patent: Nov. 17, 1987

[54] AIR/FUEL RATIO CONTROL SYSTEM INCLUDING MEANS TO WELL TIME START OF FEEDBACK

[75] Inventors: Toyoaki Nakagawa, Yokohama City; Shisei Kai, Yokosuka City, both of Japan

[73] Assignee: Nissan Motor Co., Ltd., Yokohama City, Japan

[21] Appl. No.: 835,031

[22] Filed: Feb. 28, 1986

[30] Foreign Application Priority Data

Mar. 7, 1985 [JP] Japan .................................. 60-45965

[51] Int. Cl.$^4$ ............................................. G01N 27/46
[52] U.S. Cl. ..................... 204/406; 204/412; 204/425; 204/427; 204/408; 123/440; 123/489
[58] Field of Search ................ 204/15, 412, 425, 408, 204/421–429, 406; 123/440, 489

[56] References Cited

U.S. PATENT DOCUMENTS

| 4,365,604 | 12/1982 | Sone | 204/15 |
| 4,566,419 | 1/1986 | Ninomiya | 204/15 |
| 4,609,453 | 9/1986 | Shinomura | 204/15 |

*Primary Examiner*—John F. Niebling
*Assistant Examiner*—Ben C. Hsing

*Attorney, Agent, or Firm*—Schwartz, Jeffery, Schwaab, Mack, Blumenthal & Evans

[57] ABSTRACT

The invention relates to a control system for feedback control of the air/fuel ratio in an internal combustion engine by using a solid electrolyte oxygen sensor to sense oxygen in the exhaust gas. The oxygen sensor is of the type having an oxygen concentration cell and an oxygen ion pump cell to which a pumping current is supplied to vary the partial pressure of oxygen in the exhaust gas admitted in a measurement space in the sensor. The pumping current is controlled so as to nullify a difference between the output voltage of the oxygen concentration cell and a target voltage. A signal derived from the controlled pumping current is used as an air/fuel ratio signal on the premise that a definite correlation exists between the magnitude of the pumping current and the oxygen concentration in the exhaust gas. To commence feedback control of the air/fuel ratio soon after starting the engine and after establishment of the definite correlation without unnecessary delay, the control system includes discrimination means for forming a judgment that the expected definite correlation has been established if the output voltage of the oxygen concentration cell surely falls within a predetermined tolerance range containing the target voltage. When such a judgment is formed the feedback control is immediately commenced.

5 Claims, 8 Drawing Figures

AIR/FUEL RATIO CONTROL SYSTEM INCLUDING MEANS TO WELL TIME START OF FEEDBACK

BACKGROUND OF THE INVENTION

This invention relates to a system for controlling the air/fuel ratio in an internal combustion engine, particularly an automotive engine, by using an oxygen sensor as an exhaust gas sensor to detect actual values of the air/fuel ratio. The oxygen sensor utilizes a solid electrolyte and is a combination of an oxygen concentration cell and an oxygen ion pump cell.

In the current automotive internal combustion engines, it is popular to perform feedback control of the air/fuel ratio by using an oxygen sensor comprising a solid electrolyte cell to estimate actual values of the air/fuel ratio from concentrations of oxygen in the exhaust gas. At starting the engine, however, it is customary to defer the start of the feedback control until completion of the engine warm-up or transiently accelerating operation. In this regard a recent trend is to commence the feedback control of the air/fuel ratio soon after starting the engine with a view to satisfying the demands for better fuel economy and cleaner exhaust gases. Then it becomes necessary to employ an oxygen sensor which is, as an exhaust gas sensor, responsive to changes in the air/fuel ratio in the engine over a fairly wide range including both sub-stoichiometric and super-stoichiometric regions.

Under such circumstances some kinds of oxygen sensors have been developed by modifying the well known oxygen sensor which utilizes an oxygen ion conductive solid electrolyte, such as zirconia, and functions as an oxygen concentration cell. One of the modifications is combining the oxygen concentration cell with another solid electrolyte cell of fundamentally the same construction so as to define a narrow space between the two cells. For example, U.S. Pat. No. 4,450,065 shows an oxygen sensor of this type. In this oxygen sensor the narrow space between the two solid electrolyte cells admits a fraction of the exhaust gas to be measured so that the oxygen concentration cell generates an electromotive force, viz. a voltage, the magnitude of which depends on the partial pressure of oxygen in the gas within the narrow space. The other solid electrolyte cell is used as an oxygen ion pump cell by supplying thereto a DC current, called pumping current, to transfer some oxygen ions from or into the aforementioned space through the solid electrolyte layer of this cell. The pumping current is controlled so as to nullify a difference between the output voltage of the oxygen concentration cell and a reference voltage which corresponds to the target value of the air/fuel ratio in the engine. Therefore, the actual air/fuel ratio can be estimated from the polarity and magnitude of the pumping current needed for equalizing the output voltage and the reference voltage.

For feedback control of an internal combustion engine the oxygen sensor including the oxygen ion pump cell is used in the above described manner on the premise that a definite correlation exists between the adjusted pumping current and the oxygen concentration in the exhaust gas diffused into the measurement space in the oxygen sensor. However, at starting the engine the definite correlation is not established until the solid electrolyte cells in the oxygen sensor are sufficiently heated to reach a fully active state. Even though the oxygen sensor is provided with a heater which can be energized at the time of starting the engine, a length of time elapses before establishment of the expected correlation between the pumping current and the oxygen concentration, and it is difficult to exactly predict the time of establishment of the correlation. This constitutes a difficulty in lessening the delay in starting the feedback control of the air/fuel ratio. If the feedback control is commenced soon after starting the engine without considering the time required for establishment of the expected definite correlation or by hastely and incorrectly judging that the definite correlation has already been established, the exhaust gas composition and the engine operational characteristics become worse. If the feedback control is started with an ample surplus of time for establishment of the definite correlation without trying to ascertain establishment of the correlation, still there is unnecessary delay in the start of the feedback control so that the desire for improvements in the engine performance and exhaust emission cannot fully be met.

SUMMARY OF THE INVENTION

It is an object of the present invention to provide an improved control system for feedback control of the air/fuel ratio in an internal combustion engine, which may be an automotive engine, by using an oxygen sensor of the above described type having an oxygen ion pump cell and by incorporating a discrimination means as an element of the control system to accurately and quickly detect establishment of an expected definite correlation between the pumping current adjusted in the above described manner and the concentration of oxygen in the exhaust gas within the measurement space in the oxygen sensor.

According to the invention, the aforementioned discrimination means has the function of ascertaining whether or not the output voltage of the oxygen concentration cell in the oxygen sensor is within a predetermined tolerance range containing the target value of the output voltage, and the control system commences feedback control of the air/fuel ratio if the output voltage is within that range since, if so, it is reasonable to presume that the expected definite correlation between the pumping current and the oxygen concentration has already been established.

More definitely, the invention provides a control system for feedback control of the air/fuel ratio of an air-fuel mixture supplied to an internal combustion engine, the control system comprising an oxygen sensor which is disposed in an exhaust passage of the engine and comprises a first solid electrolyte cell having an oxygen ion conductive solid electrolyte layer provided with a reference electrode on one side thereof and a measurement electrode on the opposite side, reference means for maintaining a reference gas atmosphere containing a given amount of oxygen such that the reference electrode is exposed to the reference gas atmosphere, measurement means for defining a space which provides access to the measurement electrode for gases and restrictively admitting a fraction of the exhaust gas of the engine into the space and a second solid electrolyte cell having an oxygen ion conductive solid electrolyte layer provided with a pair of electrodes in such an arrangement that an externally supplied pumping current flows through the solid electrolyte layer to cause migration of oxygen ions therethrough and to thereby cause a change in the partial pressure of oxygen in the aforementioned space, and measurement means for supplying the pumping current to the second solid electrolyte cell of the oxygen sensor while controlling the pumping current so as to render the output voltage of the first solid electrolyte cell equal to a target value and producing an air/fuel ratio signal which is representative of the magnitude of the controlled pumping current. The control system further comprises control means for producing and outputting an air/fuel mixing ratio control signal based on the air/fuel ratio signal, and this control means includes discrimination means for ascertaining whether or not the output voltage of the first solid electrolyte cell in the oxygen sensor is within a predetermined tolerance range containing the target value and suspension means for suspending outputting the air/fuel mixing ratio control signal if the output voltage is outside the predetermined tolerance range.

The air/fuel ratio control system according to the invention is very suitable for application to automotive engines. It is a matter of course that the air/fuel mixing ratio control signal produced in this system is used to regulate the rate of air intake into the engine and/or the rate of fuel feed to the engine. In this control system, establishment of a definite correlation between the pumping current controlled in the above stated manner and the partial pressure of oxygen in the exhaust gas admitted in the measurement space in the oxygen sensor can be detected accurately and quickly. Therefore, after starting the engine the commencement of feedback control of the air/fuel ratio can be timed almost optimumly. This is very favorable for fuel economy and exhaust gas purification at the early stage of the engine operation. The control means according to the invention can be embodied in a microcomputer.

DESCRIPTION OF THE PREFERRED EMBODIMENTS

Figure 1:
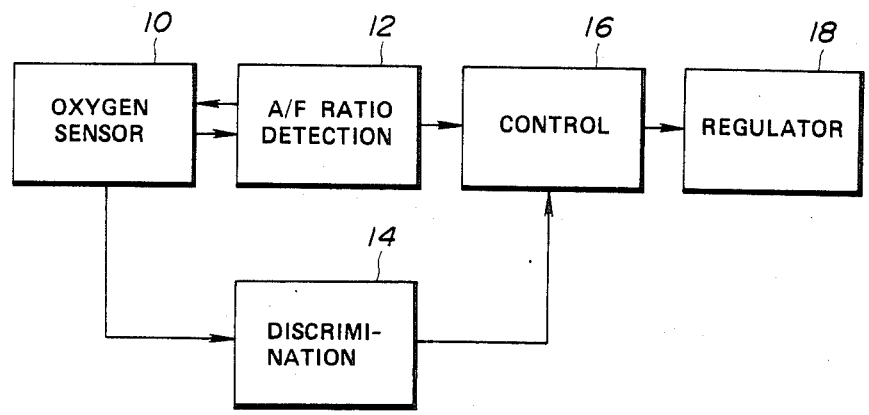
FIG. 1 is a block diagram showing the fundamental construction of an air/fuel ratio control system according to the invention.

In an air/fuel ratio control system according to the invention, the functional connections between the principal elements are as shown in FIG. 1. An oxygen sensor 10 employed in this system utilizes an oxygen ion conductive solid electrolyte and is comprised of a sensor cell which functions as an oxygen concentration cell and an oxygen pump cell which is operated by application of a current to regulate the concentration of oxygen in a chamber in which the measurement electrode of the sensor cell is exposed. The oxygen sensor 10 is disposed in the exhaust system of the internal combustion engine in which the air/fuel ratio is to be controlled.

The oxygen sensor 10 is associated with an air/fuel ratio detetection unit 12, which includes a current supply means to supply a controlled pumping current to the pump cell of the oxygen sensor 10 so as to keep the output voltage of the sensor cell at a predetermined value and a detection means to produce an air/fuel ratio signal based on the magnitude of the pumping current. In addition, the detection unit 12 has a comparison means to find deviations of the output voltage of the oxygen sensor 10 from the aforementioned predetermined value. A discrimination unit 14 also receives the output voltage of the oxygen sensor 10 to produce a signal which indicates whether the sensor output voltage is within a predetermined range or not. A control unit 16 receives the air/fuel ratio signal from the detection unit 12 along with the signal produced by the discrimination unit 14 and, when the latter signal indicates that the output voltage of the oxygen sensor 10 is within the predetermined range, produces either a fuel feed control signal or an air intake control signal to control the air/fuel ratio in the engine to the predetermined ratio based on the air/fuel ratio signal from the detection unit 12. The signal produced in the control unit 16 is supplied to an electromechanical means 18 for minutely varying the feed rate of fuel or air to the engine.

Figure 2:
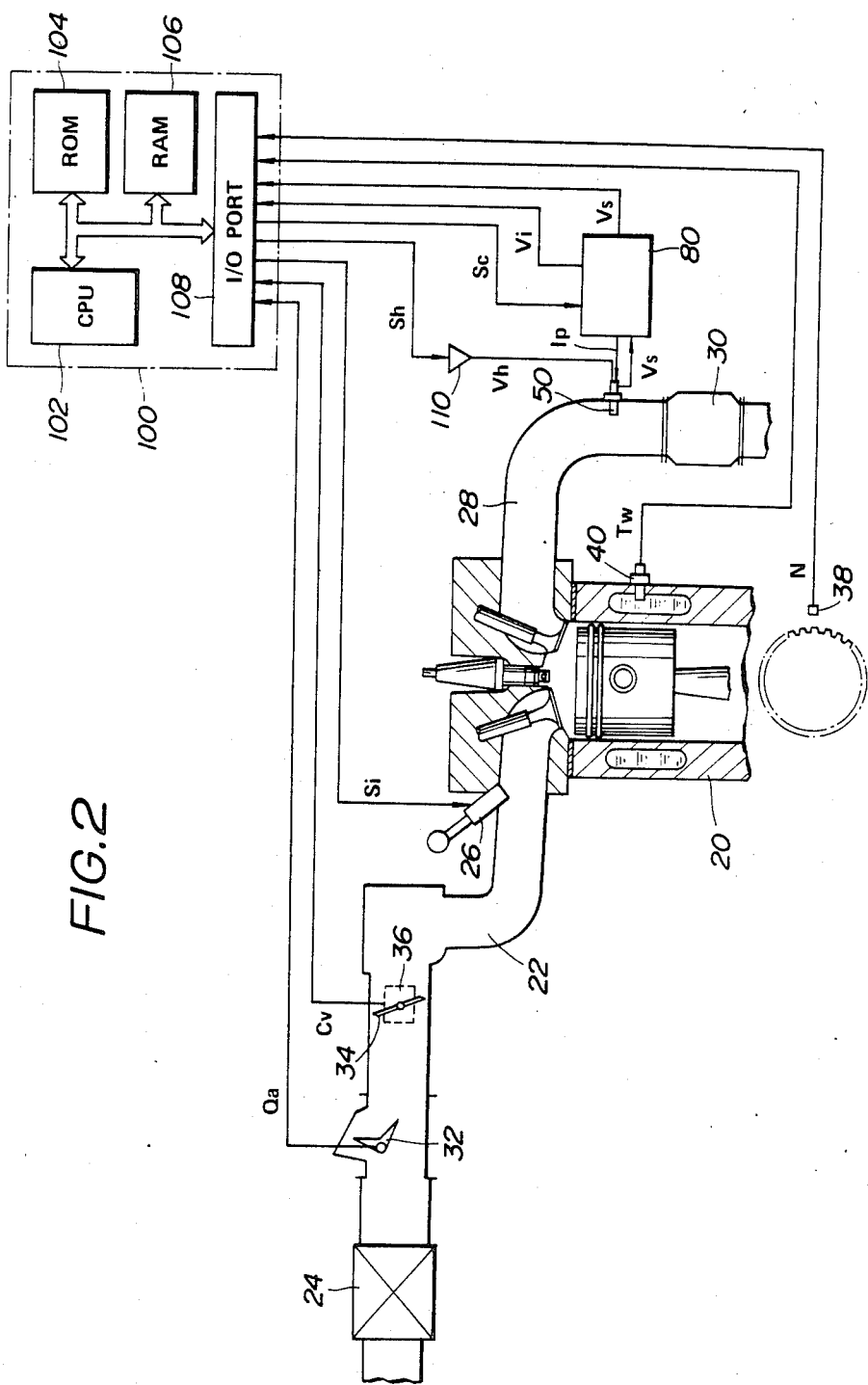
FIG. 2 is a diagrammatic illustration of an embodiment of the invention, which is an air/fuel ratio control system for an automotive engine.

As an embodiment of the invention, FIG. 2 shows an automotive internal combustion engine 20 provided with an air/fuel ratio control system which accomplishes its purpose by controlling the rate of fuel feed to the engine. In the usual manner an intake passage 22 extends from an air cleaner 24 to the combustion chambers of the engine 20, and electromagnetically operated fuel injectors 26 open into the intake passage 22. In exhaust passage 28, a catalytic converter 30 occupies an intermediate section for purifying the exhaust gases by means of a suitable catalyst such as a three-way catalyst.

In the intake passage 22 there is an airflow meter 32 which produces a signal representative of the flow rate $Q_a$ of air being taken into the engine, and a sensor 36 is coupled with throttle valve 34 to produce a signal representative of the degree of opening $C_v$ of the throttle valve 34. A crank-angle sensor 38 is provided to produce a signal representative of the engine revolving speed N. A temperature sensor 40 is disposed in the cooling water jacket to produce a signal representative of the cooling water temperature $T_w$.

An oxygen sensor 50 is disposed in the exhaust passage 28 at a section upstream of the catalytic converter 30 to estimate an actual air/fuel ratio in the combustion chambers from the concentration of oxygen in the exhaust gas. As mentioned hereinbefore with reference to FIG. 1, this oxygen sensor 50 is a combination of a sensor cell which generates an output voltage $V_s$ and an oxygen ion pump cell. An air/fuel ratio detection circuit 80, which corresponds to the item 12 in FIG. 1, supplies a controlled pumping current $I_p$ to the pump cell of the oxygen sensor 50 in response to a start signal $S_c$ sent from a control unit 100. This circuit 80 includes a comparator circuit to compare the output voltage $V_s$ of the oxygen sensor 50 with a predetermined voltage and a current detection circuit which provides a voltage signal $V_i$ representative of the magnitude of the pumping current $I_p$. The air/fuel ratio control system of FIG. 2 has a control unit 100 in which the discrimination unit 14 and control unit 16 shown in FIG. 1 are integrated. This control unit 100 is a microcomputer comprised of CPU 102, ROM 104, RAM 106 and I/O port 108. The ROM 104 stores programs of operations of CPU 102. The RAM 106 stores various data to be used in operations of CPU 102, some of which are in the form of a map or a table. The signals produced by the above described sensors 32, 36, 38 and 40 are input to the I/O port 108 along with the voltage signals $V_s$ and $V_i$ sent from the air/fuel ratio detection circuit 80. Based on the engine operating condition information gained from these input signals the control unit 100 provides a fuel injection control signal $S_i$ to the injectors 26 so as to realize an intended air/fuel ratio. Furthermore, the control unit 100 provides the aforementioned start signal $S_c$ to the air/fuel ratio detection circuit 80 at a suitable time, and from that time on, in order to use the oxygen sensor 50 for estimating the actual air/fuel ratio only under appropriate conditions. In addition, the control unit 100 produces a voltage signal called heater signal $S_h$ under specific conditions, and an amplifier 110 amplifies the heater signal $S_h$ to a heater voltage $V_h$ which is applied to a heater included in the oxygen sensor 50.

Figure 3:
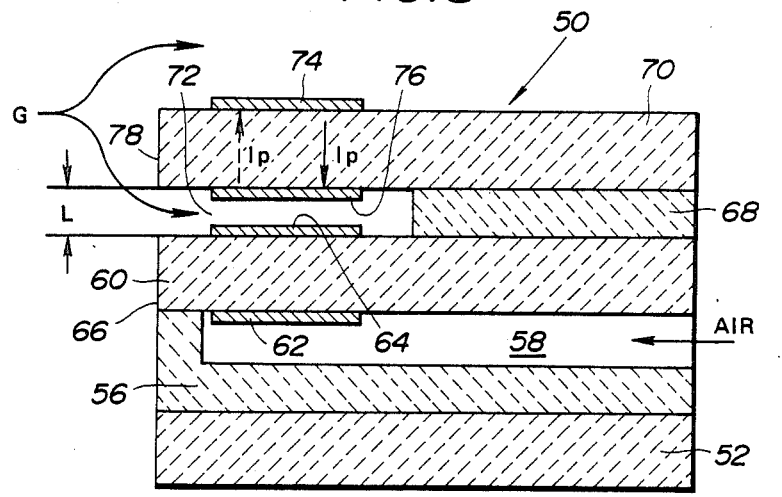
FIG. 3 is a schematic and sectional view of an oxygen sensor used in the system of FIG. 2.
Figure 4:
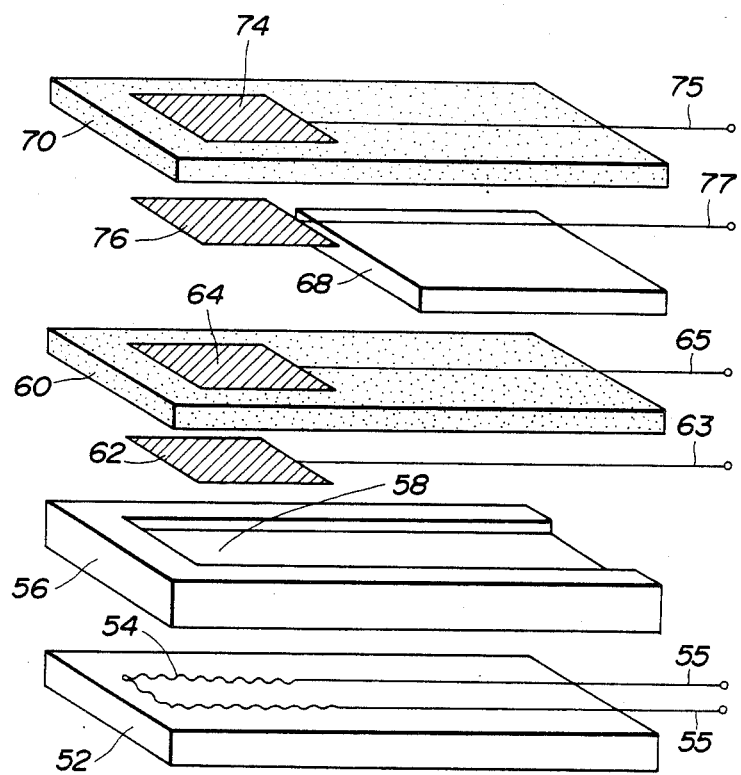
FIG. 4 is an exploded view of the oxygen sensor of FIG. 3.

The construction of the oxygen sensor 50 is, for example, as shown in FIGS. 3 and 4. This oxygen sensor 50 is a laminate-like assembly of thin layers including a substrate 52 of a ceramic material such as alumina. As shown in FIG. 4, a heater element 54 connected with leads 55 is attached to or embedded in the substrate 52. On the substrate 52 there is another ceramic board 56, which is formed with a shallow channel 58 in its top surface so as to leave undepressed marginal regions on three sides. A first layer or plate 60 of an oxygen ion conductive solid electrolyte, such as zirconia stabilized with calcia or yttria, is bonded to the ceramic board 56 so that the channel 58 in the board 56 becomes a chamber which is open to the atmosphere only at one side of the rectangular assembly. The bottom face of the solid electrolyte plate 60 is locally laid with an anode layer 62 which is to be exposed to the air admitted into the chamber 58. The top face of the solid electrolyte plate 60 is locally laid with a cathode layer 64. As shown in FIG. 4, leads 63 and 65 extend from the anode layer 62 and the cathode layer 64, respectively. A spacer sheet 68 is bonded to the solid electrolyte plate 60 so as to cover a roughly half area not containing the cathode layer 64. Usually the thickness L of the spacer 68 is about 0.1 mm. A second layer or plate 70 of an oxygen ion conductive solid electrolyte is bonded to the spacer 68 so as to lie opposite and parallel to the first solid electrolyte plate 60. As the result, a gap 72 of the given width L exists between the first and second solid electrolyte plates 60 and 70. The bottom face of the second solid electrolyte plate 70 is locally laid with a cathode layer 76, which faces to and is exposed in the gap 72. An anode layer 74 is formed on the top face of the same solid electrolyte plate 70. As shown in FIG. 4, leads 75 and 77 extend from the anode 74 and the cathode 76, respectively.

In using this oxygen sensor 50 in the air/fuel ratio control system of FIG. 2, the sensor 50 is disposed in the exhaust passage 28 such that the exhaust gas indicated by arrows G in FIG. 3 enters the gap 72 between the two solid electrolyte plates 60 and 70 while only the air (or an alternative oxygen-containing reference gas) is admitted into the chamber 58. The combination of the first solid electrolyte plate 60 and the anode and cathode layers 62 and 64 serves as an oxygen concentration cell which generates a variable electromotive force or voltage $V_s$ according to a difference in oxygen partial pressure between the air existing on the anode side and the gas G existing on the cathode side. In the following description this combination will be called a sensor cell 66.

In the oxygen sensor 50 the combination of the second solid electrolyte plate 70 and the anode and cathode layers 74 and 76 will be called a pump cell 78. When an externally supplied DC current $I_p$ flows across the solid electrolyte plate 70 from the anode 74 toward the cathode 76, there occurs migration of oxygen ions through the solid electrolyte plate 70 from the cathode side toward the anode side. Therefore, the flow of the current $I_p$ in such a direction results in extraction of some oxygen from the gas G existing in the gap 72. When the current $I_p$ flows in the reverse direction some oxygen is supplied through the solid electrolyte plate 70 to the gas G in the gap 72. Thus, the pump cell 78 functions as an oxygen ion pump. Because of the narrowness of the gap width L, considerable resistance is offered to diffusion of the exhaust gas G into the gap 72. Therefore, the transfer of oxygen from or into the gap 72 by the action of the pump cell 78 is effective for varying the partial pressure of oxygen within the gap 72. For this reason the magnitude of the output voltage $V_s$ of the sensor cell 66 can be varied by controlling the pumping current $I_p$.

The heater 54 is provided to the oxygen sensor 50 for heating both the first and second solid electrolyte layers 60 and 70 when the exhaust gas temperature is not sufficiently high since the solid electrolyte material used in the sensor 50 is usefully active only at fairly elevated temperatures.

Figure 5:
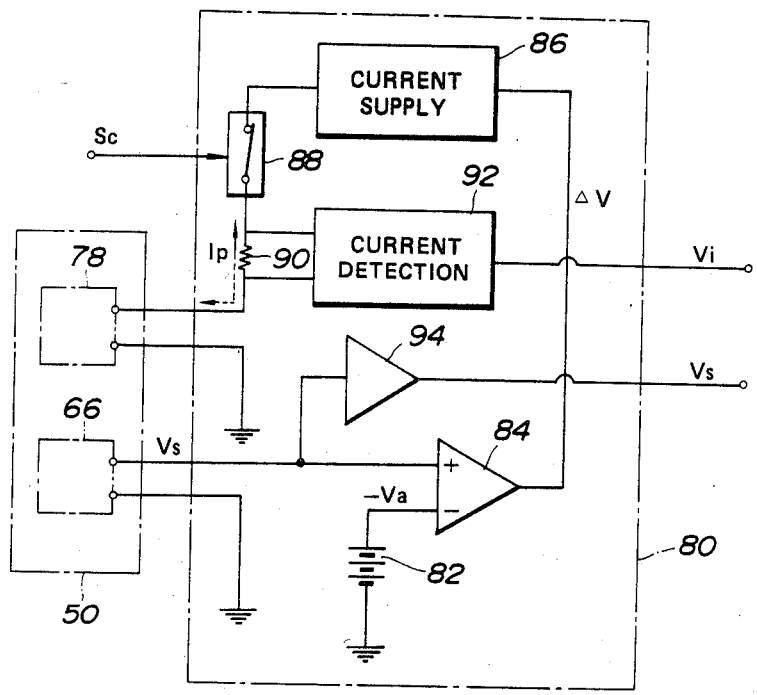
FIG. 5 is a simplified circuit diagram of an air/fuel ratio detection circuit used in the system of FIG. 2.

FIG. 5 shows the construction of the air/fuel ratio detection circuit 80 in the system of FIG. 2. The circuit 80 includes a DC power source 82 which provides a target voltage $-V_a$. A differential amplifier 84 is used to compare the output voltage $V_s$ of the sensor cell 66 of the oxygen sensor 50 with the target voltage $-V_a$ and to output a voltage signal $\Delta V$ which represents the difference $V_s - (-V_a)$. There is a current supplying circuit 86 for supplying the pumping current $I_p$ to the pump cell 78 of the oxygen sensor 50. This circuit 86 receives the output $\Delta V$ of the differential amplifier 84 and vaires the polarity and magnitude of the current $I_p$ so as to nullify the differential voltage $\Delta V$ by the function of the pump cell 78. More particularly, the current supplying circuit 86 functions so as to increase the pumping current $I_p$ when the differential voltage $\Delta V$ is positive and to decrease the current $I_p$ when $\Delta V$ is negative. In FIG. 5 the pumping current $I_p$ is positive when flowing in the direction of the solid line arrow and negative when flowing in the direction of the broken line arrow. The path of the current $I_p$ includes an analog switch 88 and a resistance 90. The analog switch 88 is normally in the open state and closes when the start signal $S_c$ is supplied from the control unit 100. The resistance 90 is used to detect the magnitude of the pumping current $I_p$ by a current detection circuit 92, which produces a voltage signal $V_i$ proportional to a voltage drop across the resistance 90. Naturally, $V_i$ is proportional to $I_p$. The air/fuel ratio detection circuit 80 includes a buffer amplifier 94 via which the output voltage $V_s$ of the oxygen sensor 50 is fed to the control unit 100.

Figure 6:
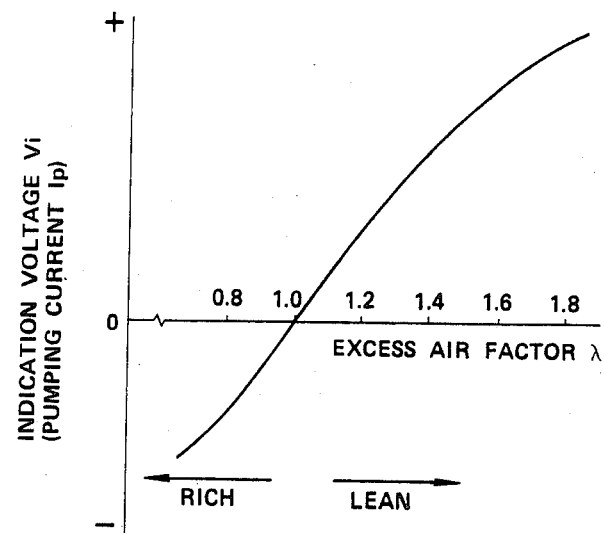
FIG. 6 is a graph showing the relationship between air/fuel ratio in the engine in FIG. 2 and a voltage signal produced in the circuit of FIG. 5.

In the air/fuel ratio detection circuit 80 the target voltage $-V_a$ is set at such a value that the output voltage $V_s$ of the oxygen sensor 50 becomes equal to $-V_a$ when the concentration of oxygen in the gas within the gap 72 in the oxygen sensor 50 is as expected under the desired air/fuel ratio condition or, in other words, when the oxygen partial pressure ratio between the anode 62 and the cathode 64 of the sensor cell 66 is as expected. Since the pumping current $I_p$ is controlled so as to nullify the difference $\Delta V$ between $V_s$ and $-V_a$ while $V_s$ is deviating from $-V_a$ by changes in the oxygen concentration in the exhaust gas G diffused into the gap 72, the current $I_p$ or indication voltage $V_i$ produced by the current detection circuit 92 varies with the actual air/fuel ratio of the mixture supplied to the engine. There is a definite relationship between the air/fuel ratio and the indication voltage $V_i$ as shown in FIG. 6, wherein the air/fuel ratio on the abscissa is represented by excess air factor ($\lambda$). Therefore, by utilizing the indication voltage $V_i$ it is possible to accurately and continuously detect the actual air/fuel ratio over a wide range including both fuel-rich conditions and lean conditions.

The operations of the control unit 100 will be described with reference to FIGS. 7 and 8 as well as FIG. 2.

Figure 7:
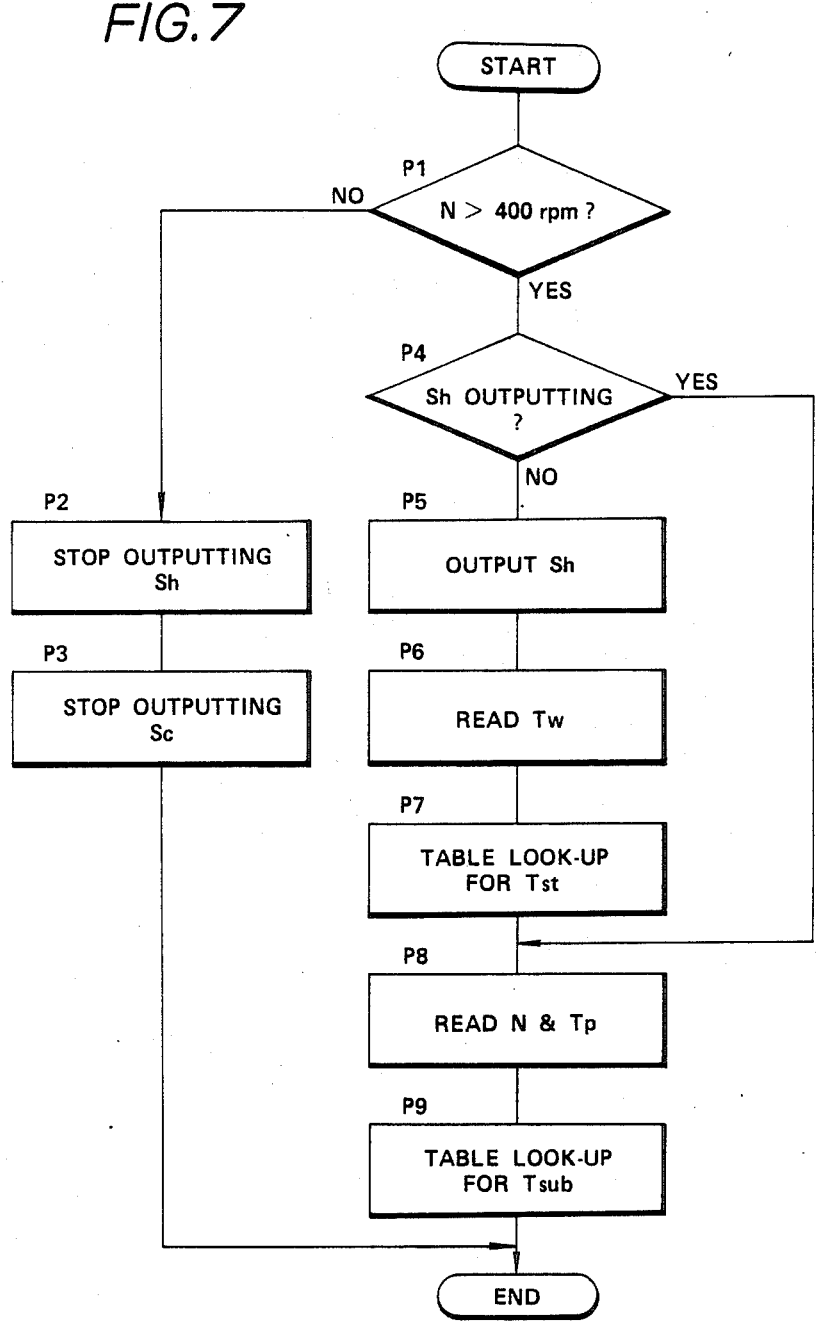
FIG. 7 is a flow chart showing a computer program stored in the control unit of the system of FIG. 2 for determining the time of starting detecting the air/fuel ratio by using the oxygen sensor.

FIG. 7 is a flow chart of one of the computer programs stored in the ROM 104 of the control unit 100. This program is for proper timing of starting the detection of air/fuel ratio. This program is assigned to a background job and is repeatedly executed at irregular intervals in spare moments from the interruption processing.

At the initial step P1, it is ascertained whether the engine 20 was already started or not by examining whether or not the engine revolving speed N is above a predetermined speed, 400 rpm in this case. If N does not exceed 400 rpm, the operation proceeds to the step P2 where output of the heater signal $S_h$ is stopped, or is kept stopped if it has already been stopped, and then to the step P3 where output of the start signal $S_c$ is stopped or kept stopped, and returns to the waiting state. If N is above 400 rpm, the operation proceeds to the step P4 where it is ascertained whether the heater signal $S_h$ is being output or not. If not, output of the heater signal $S_h$ is commenced at the step P5, and the cooling water temperature $T_w$ at that moment is read at the step P6. At the next step P7, table look-up is done based on the cooling water temperature $T_w$ to find a suitable time $T_{st}$ of commencing to output the start signal $S_c$. T is the time of starting the detection of the $T_{st}$ is the time of starting the detection of the concentration of oxygen in the exhaust gas G by using the oxygen sensor 50, and $T_{st}$ is set as a definite length of time elapsed from the moment of starting outputting the heater signal $S_h$. Optimum values of $T_{st}$ according to the cooling water temperatures $T_w$ (representative of the engine temperature) at starting of the engine are stored in the form of a data table. The value of $T_{st}$ increases as the cooling water temperature $T_w$ decreases.

At the next step P8, the engine revolving speed N and a basic amount of fuel injection $T_p$ are read in. The basic amount of fuel injection $T_p$ is computed by a separate routine (not illustrated) according to the following equation.

$$T_p = K \cdot Q_a / N$$

where K is a constant and $Q_a$ is the flow rate of air in the intake passage 22.

At the next step P9, a subtractive value $T_{sub}$ to be subtracted from the precedingly determined length of time $T_{st}$ at every time interval of a given period is found by table look-up based on the values of N and $T_p$ read at the step P8. The subtractive value $T_{sub}$ is for use in another program described hereinafter, and $T_{sub}$ increases as the exhaust gas temperature increases and as the exhaust gas flow velocity decreases. This is becuase, for some period soon after starting the engine, the flow of the exhaust gas has a cooling effect on the oxygen sensor 50 rather than a heating effect due to lowness of the exhaust gas temperature, and the cooling effect augments as the flow velocity increased.

If it is ascertained at the step P4 that the heater signal $S_h$ has already been output, the operation jumps to the step P8 to do table look-up at the step P9 to determine the subtractive value $T_{sub}$ according to the engine operating conditions. Thus, $T_{sub}$ is set at each execution of the routine of FIG. 7. Consequently, application of the heater voltage $V_h$ to the heater in the oxygen sensor 50 is commenced when the temperature in the exhaust passage 28 is rising after completion of the starting stage of the engine operation. This is favorable for durability of the oxygen sensor 50 because a sharp rise in the temperature of only the oxygen sensor 50 is avoided. If the heater in the oxygen sensor 50 is rapidly heated while the exhaust gas temperature has not sufficiently risen yet, durability of the sensor 50 will be marred by reason of local peeling of, for example, the heater element 54 from the adjacent surfaces.

Figure 8:
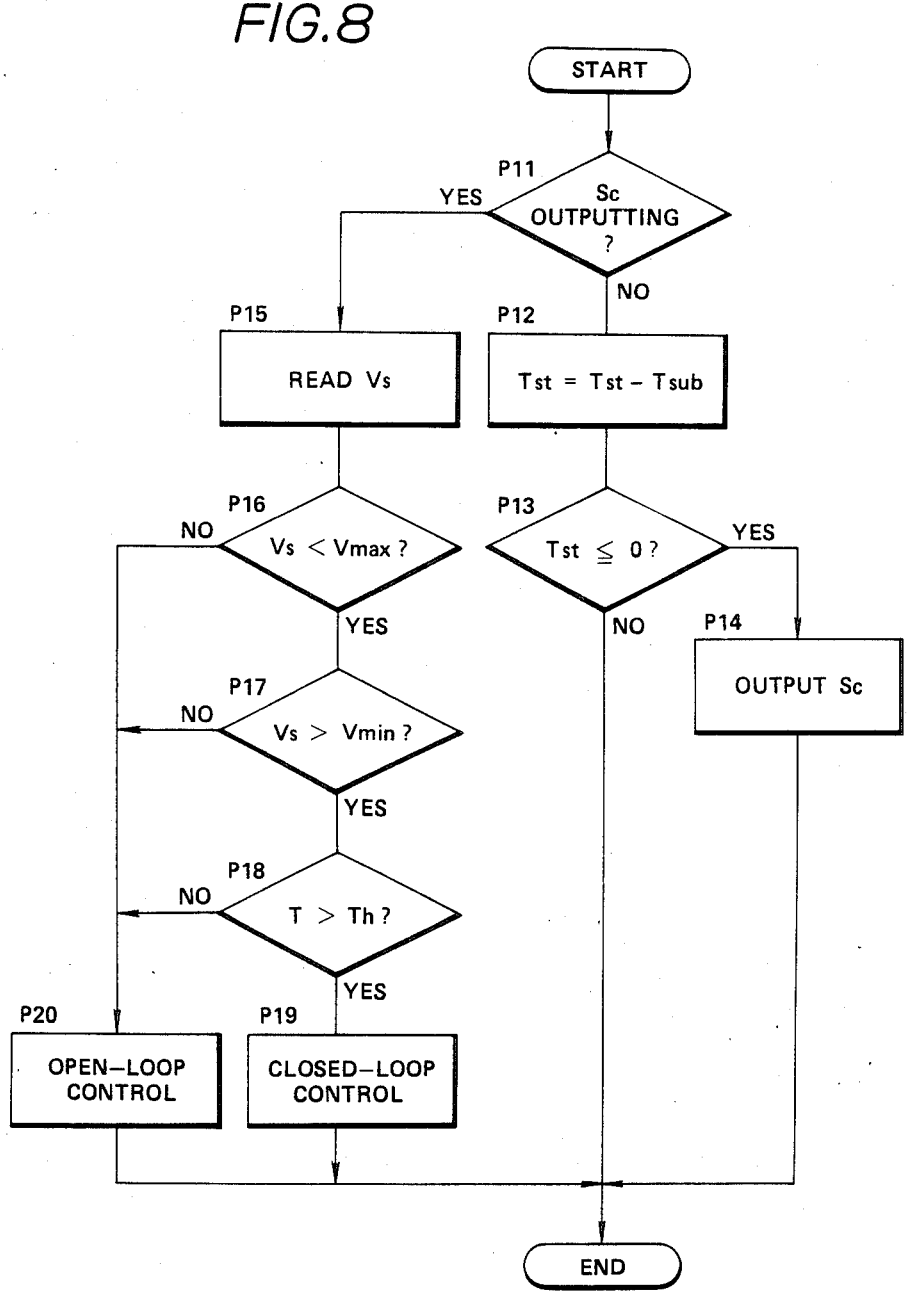
FIG. 8 is a flow chart showing another computer program stored in the same control unit for determining the time of starting feedback control of fuel feed into the engine.

FIG. 8 is a flow chart of another program stored in the ROM 104. This program is for starting the feedback control of fuel injection to maintain the desired air/fuel ratio. This program is executed at every time interval of a given period. For example, the program may be executed once with every revolution of the engine.

At the initial step P11 it is ascertained whether the start signal $S_c$ is being output or not. If not, the operation proceeds to the step P12 where the starting time $T_{st}$ is computed according to the following equation.

$$T_{st} = T_{st}' - T_{sub}$$

where $T_{st}'$ is the length of time determined at the preceding execution of the same routine.

At the next step P12, it is examined whether the value of $T_{st}$ has reached zero or not. If the value of $T_{st}$ is zero or negative, output of the start signal $S_c$ is commenced at the step P14. Then the air/fuel ratio detection circuit 80 begins to supply pumping current $I_p$ to the oxygen sensor 50 so that detection of air/fuel ratio starts. Since the solid electrolyte material in the oxygen sensor 50 has already been heated to a sufficient extent by both the heat of the exhaust gas and the heat generated by the included heater and accordingly is in a fully active state, the initial magnitude of the pumping current $I_p$ does not become excessively great. This is favorable for durability of the oxygen sensor 50. In known control systems using the same oxygen sensor the supply of the pumping current to the oxygen sensor is started simultaneously with starting of the engine and, therefore, before the solid electrolyte material assumes an active state. In such cases the initial magnitude of the pumping current becomes excessively great so that deterioration of the pump cell in the oxygen sensor is accelerated. If the value of $T_{st}$ is greater than zero at the step P13, the operation returns to the initial step P11 without proceeding to the step P14, and the routine from the step P11 to the step P13 is repeated until the value of $T_{st}$ becomes zero or negative.

If the start signal $S_c$ has already been output at the step P11 the operation proceeds on the route of steps P15 to P19, in order to make a judgment whether proper correlation between the pumping current $I_p$ and the concentration of oxygen in the gas within the gap 72 in the oxygen sensor 50 has already been established. Such correlation will be referred to as $I_p$-$O_2$ correlation. At the step P15 the oxygen sensor output voltage $V_s$ is read. At the steps P16 and P17 the output voltage $V_s$ is compared with a predetermined boundary value $V_{max}$ and with another predetermined boundary value $V_{min}$, respectively. The comparisons are for the purpose of ascertaining whether or not the output voltage $V_s$ takes a value within a predetermined tolerance range containing the target value $-V_a$ as the middle point. That is, $V_{max}$ is slightly higher than $-V_a$ and $V_{min}$ slightly lower than $-V_a$. If $V_s$ is higher than $V_{min}$ and lower than $V_{max}$ it is permissible to presume that the output of the oxygen sensor 50 has become stable. If so, the operation proceeds to the step P18 where it is ascertained whether or not a period of time T over which the output of the sensor 50 was confirmed to be stable has already exceeded a predetermined criterion length of time $T_h$. For example, $T_h$ is set between 0.1 sec and 10 sec. If T is longer than $T_h$ it is permissible to presume that proper $I_p$-$O_2$ correlation has already been established. Then, the operation proceeds to the step P19 to commence the feedback control of the air/fuel ratio by controlling the amount of fuel injection.

If $V_s$ is not higher than $V_{min}$ at the step P16 or not lower than $V_{max}$ at the step P17, it is impermissible to presume that the output of the oxygen sensor 50 has become stable. Then, the operation proceeds to the step P20 to continue open-loop control of the air/fuel ratio. If T is not longer than $T_h$ at the step P18, it is presumed that proper $I_p$-$O_2$ correlation has not been established yet so that the operation proceeds to the step P20 to continue the open-loop control.

In the above described manner, the air/fuel ratio control system of FIG. 2 carries out a series of preliminary operations to ascertain establishment of proper $I_p$-$O_2$ correlation before starting feedback control of air/fuel ratio. The feedback control is accomplished with very high accuracy even at the beginning stage of the control because, once the feedback control is started, accurate information on the actual air/fuel ratio can always be gained. In this air/fuel ratio control system using the above described computer program, the ascertainment of establishment of proper $I_p$-$O_2$ correlation can accurately be achieved within almost the irreducible minimum of time following the start of the engine operation. Such functions of this control system are very effective for prevention of worsening of the exhaust gas composition in a period soon after starting the engine and also for improvement of the performance and driveability of the engine.

The oxygen sensor for use in this invention is not limited to the particular one shown in FIGS. 3 and 4. A wide selection can be made among conventional or recently developed oxygen sensors that utilize an oxygen ion conductive solid electrolyte and comprise a combination of an oxygen concentration cell using a reference gas which contains a given amount of oxygen and an oxygen ion pump cell to which a controlled pumping current is supplied to vary the partial pressure of oxygen within a restricted space which provides access to a measurement electrode of the concentration cell. Mechanically, the two cells in the oxygen sensor may be constructed in any form and may be integrated into a seemingly single-element device.

What is claimed is:

1. A control system for feedback control of the air/fuel ratio of an air-fuel mixture supplied to an internal combustion engine, the control system comprising:

an oxygen sensor which is disposed in an exhaust passage of the engine and comprises a first solid electrolyte cell having an oxygen ion conductive solid electrolyte layer provided with a reference electrode on one side thereof and a measurement electrode on the opposite side, reference means for maintaining a reference gas atmosphere containing a given amount of oxygen such that said reference electrode is exposed to said reference gas atmosphere, measurement means for defining a space which provides access to said measurement electrode for gases and restrictively admitting a fraction of the exhaust gas of the engine into said space and a second solid electrolyte cell having an oxygen ion conductive solid electrolyte layer provided with a pair of electrodes in such an arrangement that an externally supplied pumping current flows through the solid electrolyte layer to cause migration of oxygen ions therethrough and to thereby cause a change in the partial pressure of oxygen in said space;

sensor means to detect the temperature of the engine;

means for outputting a detection start signal after the lapse of a predetermined length of time from the start of the engine, said predetermined length of time being based upon the temperature of the engine, received from said sensor means, and decreasing as the detected temperature of the engine increases;

detection means for supplying said pumping current to said second solid electrolyte cell in said oxygen sensor while controlling said pumping current so as to render the output voltage of said first solid electrolyte cell equal to a target value and producing an air/fuel ratio signal which is representative of the magnitude of the controlled pumping current, said detection means comprising means for suspending the supply of said pumping current to said second solid electrolyte cell in said oxygen sensor until receiving said detection start signal from said means for outputting a detection start signal; and control means for producing and outputting an air/fuel mixing ratio control signal based on said air/fuel ratio signal, said control means comprising discrimination means for ascertaining whether or not said output voltage is within a predetermined tolerance range containing said target value and suspension means for suspending outputting said air/fuel mixing ratio control signal if said output voltage is outside said predetermined tolerance range.

2. A control system according to claim 1, wherein said discrimination means has the function of repeatedly examining said output voltage, and said suspension means stops suspending outputting said air/fuel mixing ratio control signal when said output voltage continues to fall within said predetermined tolerance range for a period longer than a predetermined period.

3. A control system according to claim 1, further comprising a sensor to detect the flow rate of air taken into the engine and another sensor to detect the revolving speed of the engine, said control system further comprising means for decreasing said length of time as the detected flow rate of air decreases and as the detected revolving speed of the engine decreases.

4. A control system according to claim 1, wherein said oxygen sensor further comprises a heater, said control means further comprising means for energizing said heater after starting the engine before outputting said detection start signal.

5. A control system according to claim 1, wherein said control means comprises a microcomputer.

* * * * *